(12) United States Patent
Di Palma et al.

(10) Patent No.: US 8,858,497 B2
(45) Date of Patent: Oct. 14, 2014

(54) DEVICE AND METHOD FOR REMOVING MATERIAL FROM A HOLLOW ANATOMICAL STRUCTURE

(75) Inventors: Giorgio Di Palma, West Valley City, UT (US); William A. Cartier, Hampton, NY (US); William Appling, Granville, NY (US); William C. Hamilton, Jr., Queensbury, NY (US)

(73) Assignee: Angio Dynamics, Inc., Latham, NY (US)

( * ) Notice: Subject to any disclaimer, the term of this patent is extended or adjusted under 35 U.S.C. 154(b) by 465 days.

(21) Appl. No.: 13/274,163

(22) Filed: Oct. 14, 2011

(65) Prior Publication Data

US 2012/0059356 A1 Mar. 8, 2012

Related U.S. Application Data

(63) Continuation-in-part of application No. 13/226,538, filed on Sep. 7, 2011.

(60) Provisional application No. 61/380,513, filed on Sep. 7, 2010, provisional application No. 61/383,971, filed on Sep. 17, 2010, provisional application No. 61/388,669, filed on Oct. 1, 2010, provisional application No. 61/393,517, filed on Oct. 15, 2010, provisional application No. 61/422,806, filed on Dec. 14, 2010.

(51) Int. Cl.
*A61M 29/00* (2006.01)
*A61B 17/221* (2006.01)
*A61M 25/00* (2006.01)
*A61B 17/22* (2006.01)

(52) U.S. Cl.
CPC ........ *A61B 17/221* (2013.01); *A61B 2017/2212* (2013.01); *A61M 25/007* (2013.01); *A61M 25/0071* (2013.01); *A61M 25/0069* (2013.01); *A61B 2017/22082* (2013.01); *A61B 2017/2215* (2013.01)
USPC ........................................... 604/105; 606/200

(58) Field of Classification Search
CPC ................ A61F 2/01; A61F 2002/011; A61F 2002/016; A61B 17/221; A61B 17/22031; A61B 17/1214; A61B 2017/22082; A61B 2017/22034; A61B 2017/22038; A61B 2017/22084; A61B 2217/005; A61B 2017/22079
USPC ........................................... 606/200; 604/105
See application file for complete search history.

(56) References Cited

U.S. PATENT DOCUMENTS

| | | | |
|---|---|---|---|
| 6,280,413 B1 | 8/2001 | Clark et al. | |
| 2002/0188276 A1* | 12/2002 | Evans et al. | 604/509 |
| 2003/0199890 A1* | 10/2003 | Dubrul et al. | 606/159 |
| 2006/0189930 A1 | 8/2006 | Lary et al. | |
| 2006/0200191 A1* | 9/2006 | Zadno-Azizi | 606/200 |

* cited by examiner

*Primary Examiner* — Kevin C Sirmons
*Assistant Examiner* — Deanna K Hall
(74) *Attorney, Agent, or Firm* — Peter J. Flora

(57) ABSTRACT

A medical device for removing a material from a hollow anatomical structure is provided. The device includes a radially expandable capture member. The device includes a treatment segment that is positioned distally of the capture member in use and having at least one exit port adapted for delivering a fluid agent to the material. The device includes an embolic capture device that is positioned distally of the treatment segment in use and including a radially expandable filter for capturing a part of the material which travels downstream of the treatment segment. Additionally, a method is provided herein for infusing, injecting, distributing, or releasing an intended fluid into a hollow anatomical structure.

20 Claims, 15 Drawing Sheets

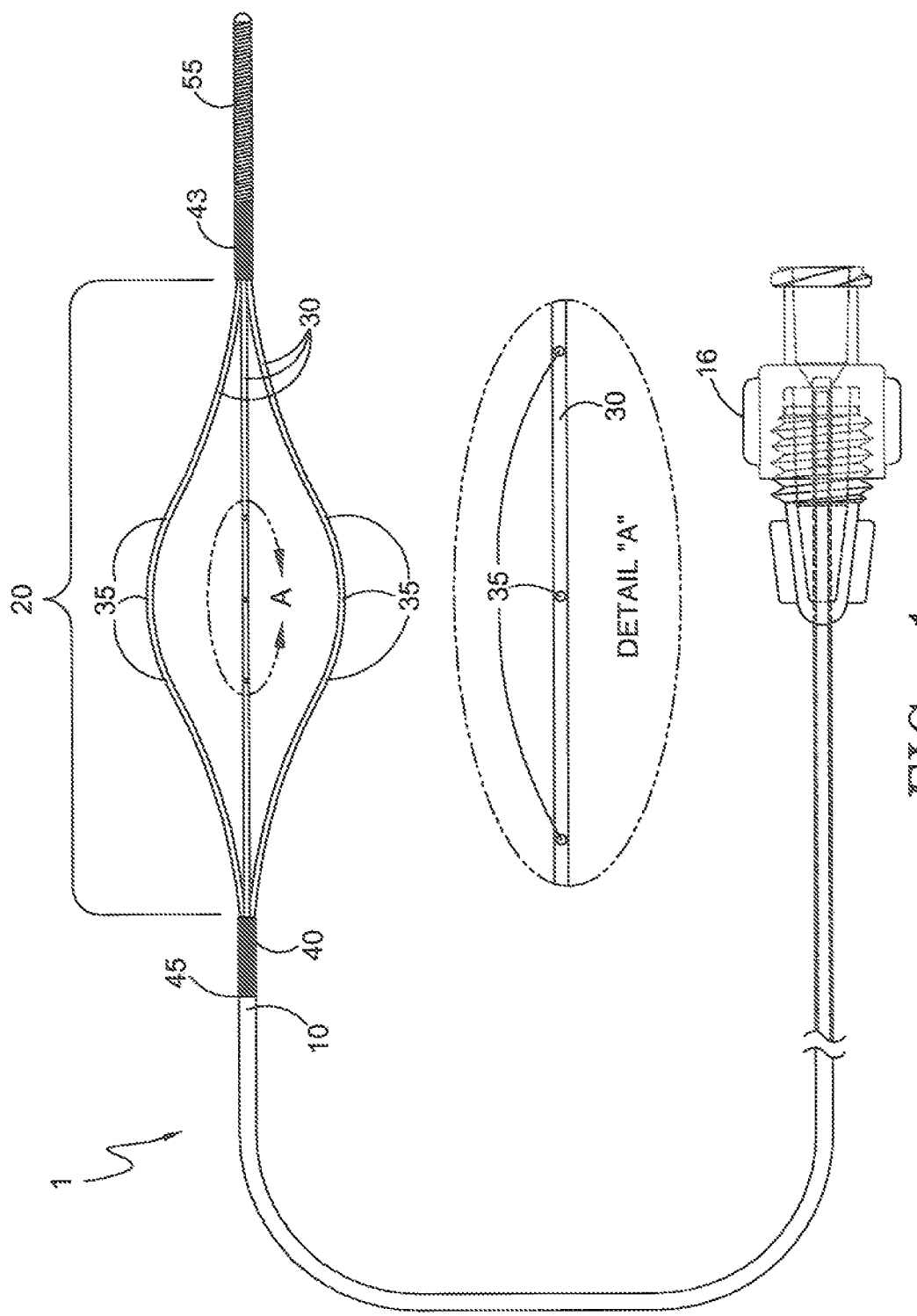

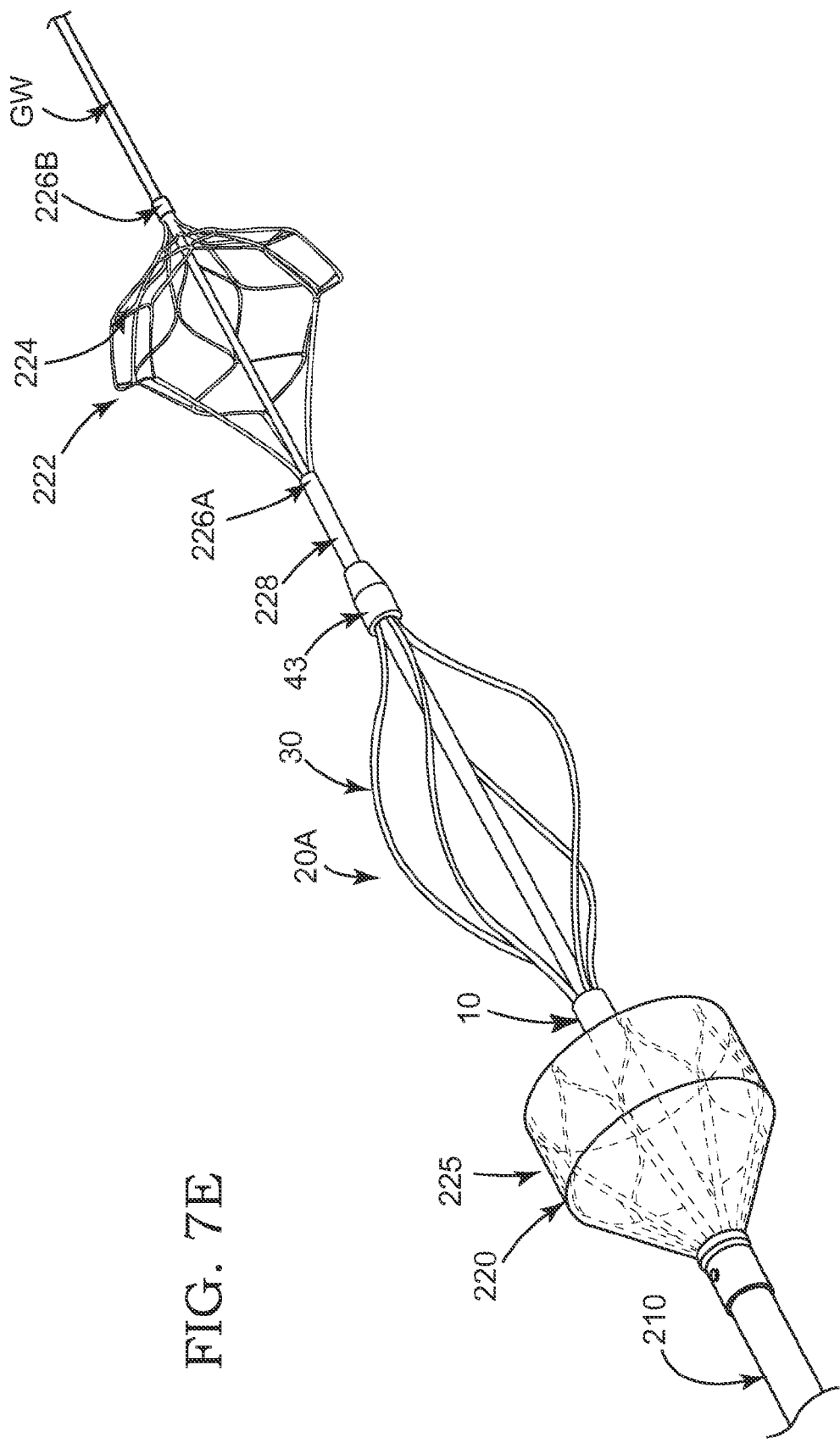

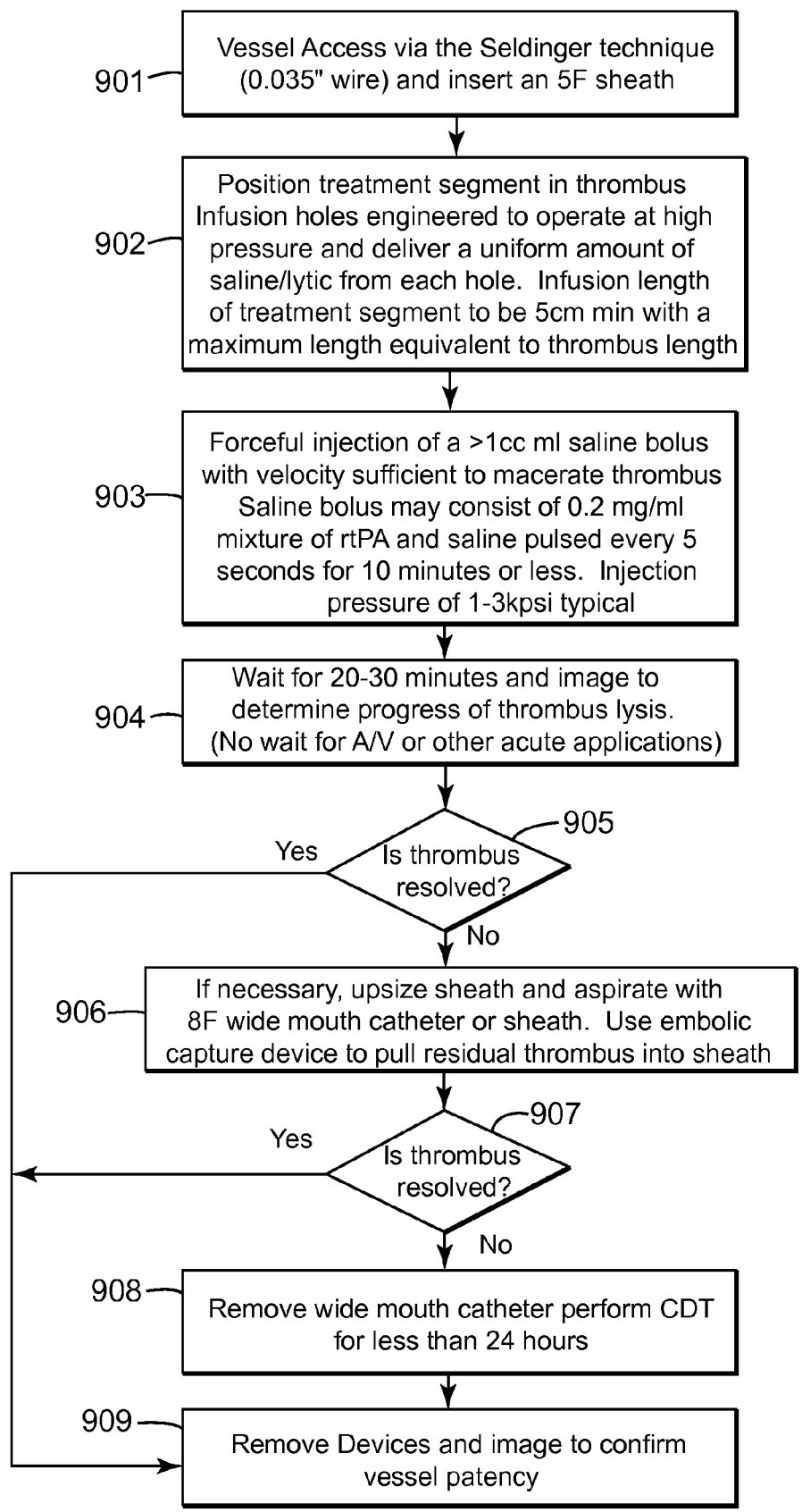

DEVICE AND METHOD FOR REMOVING MATERIAL FROM A HOLLOW ANATOMICAL STRUCTURE

CROSS REFERENCE TO RELATED APPLICATIONS

This application is a continuation-in-part of application Ser. No. 13/226,538, filed Sep. 7, 2011, which claims the benefit of U.S. Provisional Application No. 61/380,513, filed Sep. 7, 2010, U.S. Provisional Application No. 61/383,971, filed Sep. 17, 2010, and U.S. Provisional Application No. 61/388,669, filed Oct. 1, 2010, all of which are incorporated herein by reference.

This application also claims priority under 35 U.S.C. §119 (e) to U.S. Provisional Application No. 61/393,517, filed Oct. 15, 2010, and U.S. Provisional Application No. 61/422,806, filed Dec. 14, 2010, all of which are incorporated herein by reference.

FIELD OF THE INVENTION

The present invention relates generally to devices for delivering a fluid, drugs or other medical preparations to a site within a patient's body. More specifically, the invention relates to an elongated device that delivers fluid, drugs or other medical preparations to a site within a lumen of a blood vessel or another cavity or lumen within a patient's body and to mechanically treat the targeted area.

SUMMARY OF THE DISCLOSURE

According to the principles of the present invention, a medical device for removing material from a hollow anatomical structure is provided. The device includes a radially expandable capture member. The device includes a treatment segment that is positioned distally of the capture member in use and having at least one exit port adapted for delivering a fluid agent to the material. The device includes an embolic capture device that is positioned distally of the treatment segment in use and including a radially expandable filter for capturing a part of the material which travels downstream of the treatment segment.

A method for removing material from a hollow anatomical structure is provided, which includes the following steps. A removal device is inserted, which includes a radially expandable capture member, a treatment segment having at least one exit port and an embolic capture device having a radially expandable filter. The treatment segment is positioned near the material such that the expanded filter is positioned distally of the treatment segment and the expanded capture member is positioned proximally of the treatment segment, the expanded filter capturing a part of the material which travels downstream of the treatment segment. A fluid agent is injected to the material through the exit port. The treatment segment is received in the expanded capture member. The embolic capture device is received in the expanded capture member.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 1 is a plan view of the fluid delivery device of the current invention shown with the infusion segment in an expanded position.

FIG. 7A illustrates the device prior to deployment of the infusion segment. FIG. 7B illustrates the device after expansion of the infusion segment.

FIG. 7E is a partial isometric view of another embodiment of the fluid delivery device including an embolic protection device.

FIG. 9 shows a flow chart of a method for removing a thrombus from a blood vessel according to one embodiment of the invention.

DETAILED DESCRIPTION OF THE INVENTION

Figure 2A:
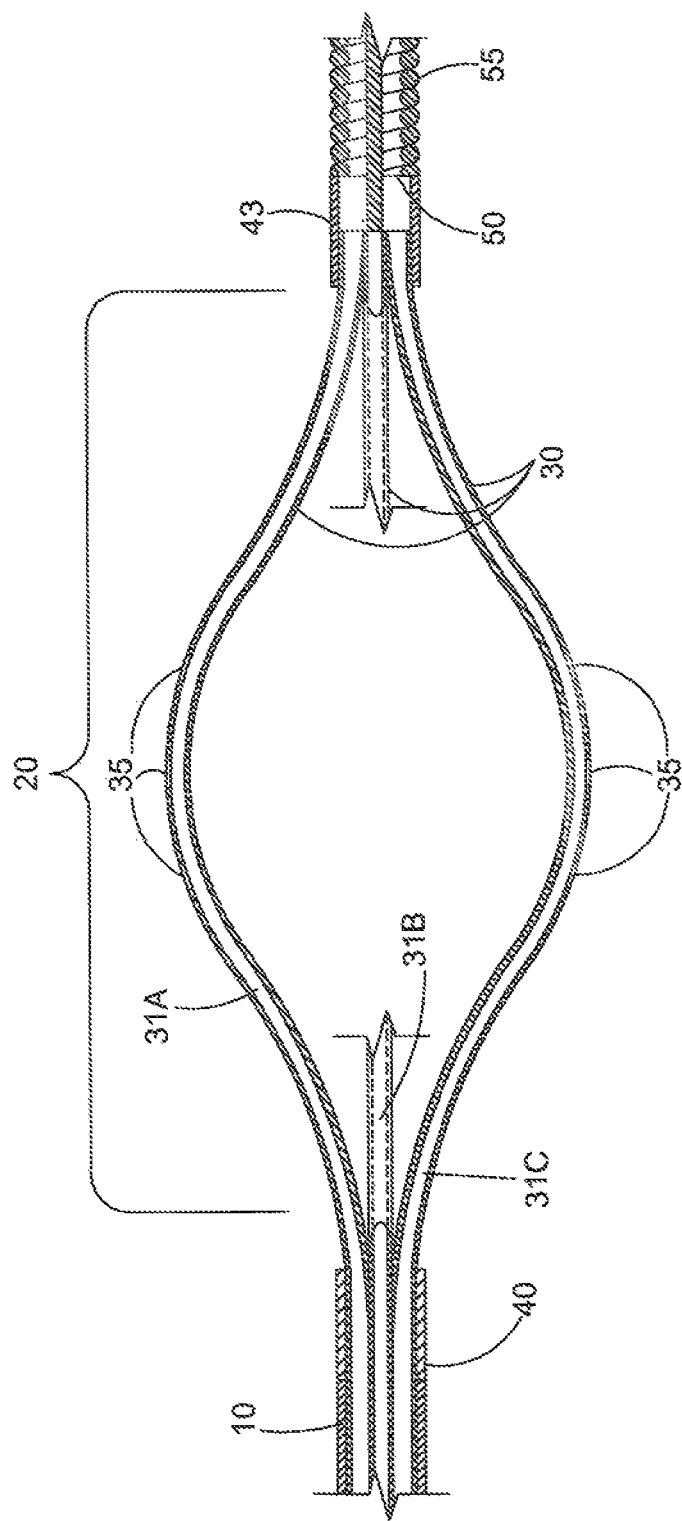
FIG. 2A is a partial enlarged cross-sectional view of the expanded infusion segment.

The present invention can be understood more readily by reference to the following detailed description and the examples included therein and to the figures and their previous and following description. The drawings, which are not necessarily to scale, depict selected preferred embodiments and are not intended to limit the scope of the invention. The detailed description illustrates by way of example, not by way of limitation, the principles of the invention.

The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

The fluid delivery and treatment device of the present invention allows a user to deliver a desired drug to the outermost edges of a clot which has formed against the vessel wall. This manner of treatment is desired in the treatment of clots because this will break the clot away from the vessel wall and help prevent the clot from forming again after the treatment. In additional to controlling the direction and location of the delivered fluid, the fluid delivery and treatment device allows the user to control the pressure of the fluid, the flow rate, and also the manner in which the fluid is delivered, such as pulse spray or a constant flow.

According to one embodiment, the invention comprises a fluid delivery and treatment device for delivering medicinal fluids to a body lumen. The device comprises a hollow member having a proximal and distal end with an expandable infusion/treatment segment disposed at the distal end. As used herein, the term "proximal" denotes the direction closer to the operator and the term "distal" denotes the direction closer to (inserted into) the patient. The expandable infusion/treatment segment is comprised of expandable infusion arms that have fluid infusion ports along its surface for fluid to exit. The expandable infusion/treatment segment is attached to the distal end of the hollow member.

A method of use of a fluid delivery and treatment device for delivering fluids to a lumen is described herein. According to one embodiment, the method begins with inserting the device having a hollow member that has a proximal and distal end into a lumen. The expandable infusion/treatment segment is expanded and fluid is delivered to the treatment site. Upon completion of treatment, the expandable infusion/treatment segment is collapsed and removed from the vessel.

Referring now in detail to the drawings, in which like reference numerals indicate like parts or elements throughout the several views, in various embodiments, presented herein is a fluid delivery and treatment device intended for the delivery of fluids within an anatomic lumen or cavity and treatment of the desired region.

Referring to FIG. 1, a fluid delivery and treatment device 1 for introducing material into the vascular system or other tubular anatomical structure is provided herein. Device 1, shown in an expanded or deployed state, is comprised of a proximal hub 16, an elongated hollow member 10, an expandable infusion segment 20 and a leading flexible tip 55. The expandable infusion segment 20 is comprised of a plurality of infusion arms 30 which each contain at least one infusion port 35 as shown in Detail "A". The expandable infusion segment 20 is attached to elongated shaft 10 by proximal collar 40 and to the leading flexible tip 55 by distal collar 43.

The proximal most end of the hollow member 10 may be fitted with a removable hub 16 to allow attachment to an injection source or device. The hub 16 can also be removed to allow the device 1 to be inserted through another treatment device. For example, the hub 16 may be removed so that a catheter can be back loaded over the proximal most end of the device, such as the subsequent placement of another type of interventional device.

Figure 2B:
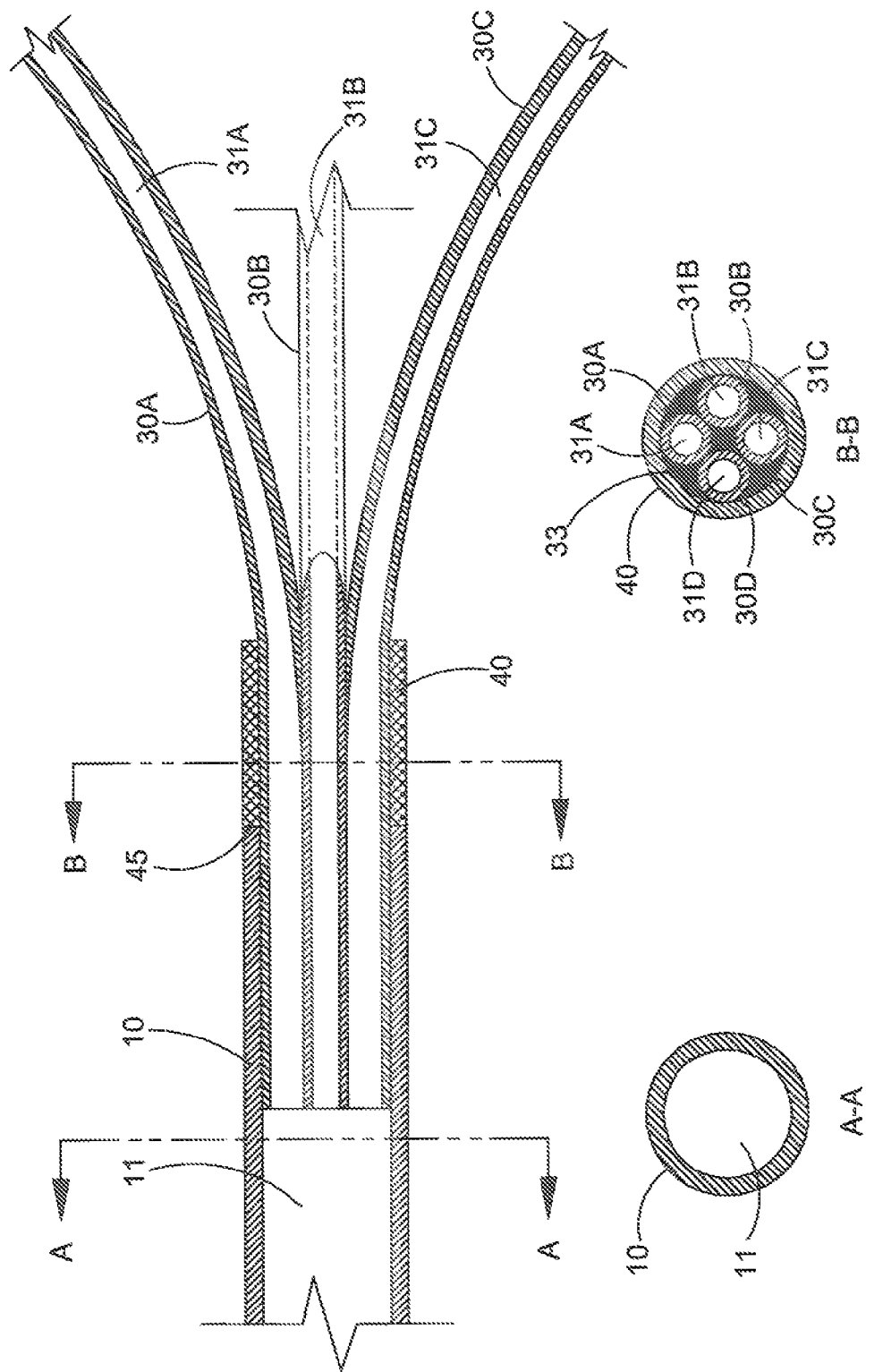
FIG. 2B is a partial enlarged cross-sectional view of the proximal portion of the expanded infusion segment.

FIG. 2A depicts a partial enlarged longitudinal cross-sectional view of the expanded infusion segment. Through lumen 11 of elongated hollow member 10 (as shown in cross-section A-A of FIG. 2B) transitions into a plurality of dedicated infusion arm lumens 31A, 31B, 31C and 31D (lumen 31D is not visible in FIG. 2A-2B). Elongated hollow member 10 is attached to collar 40 which extends distally over and coaxially surrounds the plurality of infusion arms 30A-D as shown in cross-section B-B of FIG. 2B. Elongated hollow member 10 terminates at location 45 where it abuts against the proximal end of collar 40. As shown in cross-section B-B, proximal collar 40 extends distally over and coaxially surrounds the plurality of infusion arms 30A-D. Proximal sections of arms 30A-D are held in place within shaft 10 and collar 40 by an adhesive or bonding agent 33. Other techniques known in the art such as welding or over-molding may be used.

Figure 2C:
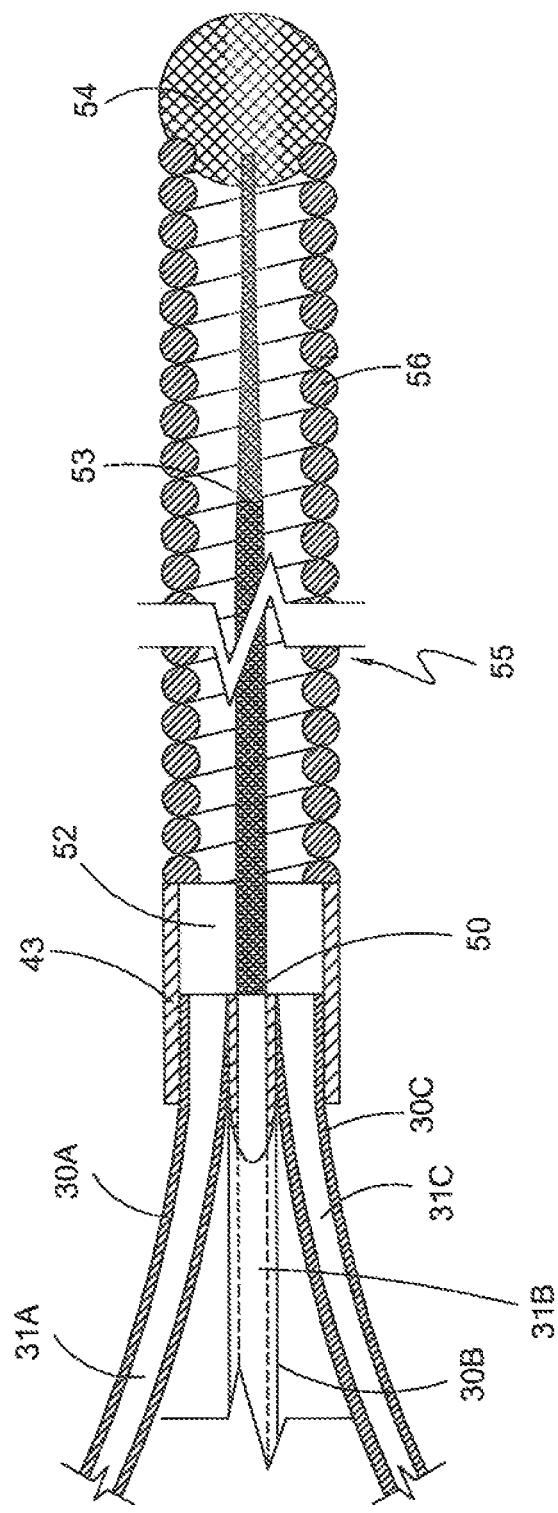
FIG. 2C is a partial enlarged cross-sectional view of the distal portion of the expanded infusion segment.

FIG. 2C depicts a partial enlarged longitudinal cross-sectional view of the distal portion of the expanded infusion segment 20 with leading flexible tip 55. Dedicated infusion arms 30A-D extend distally in a radially inward direction to meet distal collar 43 where each infusion arm is held in place by collar 43 which coaxially surrounds the plurality of arms. Each infusion lumen 31A-D terminates at plug 52. Plug 52 also houses an internal mandrel wire 53 which extends distally through the flexible tip 55 to weld ball 54. A spring coil 56, which is positioned in a spiral fashion around mandrel wire 53, provides a leading "floppy" tip as is known in the art. Flexible tip 55 facilitates tracking and advancement of device 1 through the vessel or alternatively through the lumen of a catheter or other treatment device. In one embodiment, the flexible tip 55 is approximately 1-2 centimeters in length. The coil portion and distal end weld ball may define an outer diameter of between 0.014-0.045". Alternatively, an embodiment may be built on a catheter platform between 3 French (0.039") to 20 French (0.262").

In this first embodiment, the device is sized appropriately so it can be inserted into a procedural catheter or sheath. As an example, the hollow member 10 may be comprised of a flexible hollow wire material which has an outer diameter of approximately 0.034-0.037". Furthermore, the radius of the expandable infusion/treatment segment 20 in its compressed state would be the same size as the outer diameter of the hollow member, approximately 0.034-0.037". The purpose of having the hollow member 10 and the expandable infusion/treatment segment 20 in its compressed state of approximately 0.034'-0.037' is to provide for advancement through a standard 0.035-0.038" catheter lumen. These ranges are merely an example to show that in this embodiment the outer diameter of the hollow member 10 will be less than the procedure catheter or sheath lumen which in turn will allow for proper advancement of the device 1.

In operation, infusion device 1 may introduced into the target vessel or other anatomical site using minimally invasive access techniques known in the art. In one embodiment, the device is comprised of a medical grade metal such as Nitinol and dimensioned with an outer diameter of 0.035" so as to be capable of being introduced through a standard catheter. The leading flexible tip 55 facilitates advancement of the device through the vessel to the targeted treatment site. Once positioned, a constraining sleeve or catheter (not shown) is retracted to deploy the infusion segment in an expanded position as shown in FIG. 1. Medicinal fluid may then be introduced through hub 16 (FIG. 1). The fluid travels distally through the common through lumen 11 of elongated hollow member 10 to the expanded infusion segment 20 where fluid exits through the plurality of ports 35 into the targeted treatment site. Specifically, fluid flows through lumen 11 and is directed into the dedicated lumens 31A-D of expanded infusion arms 30A-D. Fluid flows distally through each dedicated arm lumen exiting through the plurality of ports 35 so as to come in contact with targeted thrombus or other treatment target.

In another aspect of the invention, the infusion segment is not self-expanding when unconstrained by a sleeve, but rather may be mechanically adjustable to various diameters. For example, a tension wire extending through the shaft from the hub may be used to adjust the deployment diameter of the infusion segment. The operator may mechanically expand the infusion segment to a desired diameter before infusing fluid. In yet another embodiment, a self-expanding design is contemplated using a sleeve or catheter to control the expanded diameter of the infusion segment. The diameter may be adjusted by the operator using a sleeve or catheter which may be advanced over and retracted from the infusion segment to adjust the outer diameter.

In one example of treating a thrombus, the device is advanced to the treatment area with the infusion segment positioned within the thrombus mass. Using the tension wire or other mechanical adjustment means, the infusion segment is expanded to a small diameter and fluid is then dispersed through the exit ports into the inner core of the thrombus mass. In some cases, fluid may be delivered without expanding the infusion segment at all. Subsequent adjustment of the infusion segment to a larger diameter followed by re-infusion of fluid through the ports will cause the agent to be dispersed further through the clot mass. Using this incremental expansion method, the therapeutic agent may be dispersed homogenously throughout the clot mass, ultimately reaching the vessel wall. Alternatively, the infusion segment may be positioned within the clot and then expanded to a maximum profile for the infusion of the lytic agent to the outer clot mass first.

In one aspect of the invention, the infusion delivery device may also be used to mechanically disrupt and/or abrade the targeted tissue by manipulating the expanded infusion segment. The device may be rotated around its longitudinal axis and/or by repeatedly advancing and retracting the infusion segment through the targeted area to macerate the thrombus and to further disperse the medicinal agent within the thrombus volume.

In yet another embodiment, the infusion device can be used to deliver a sclerosant agent for the treatment of varicose veins. Sclerosant agents damage the vessel wall, causing the vein to collapse. One example of such an agent is Sotradecol® sclerosant. When treating a vein with sclerosant, it is important to deliver the drug directly to vessel wall itself rather than directing the fluid in the vessel lumen and blood. Sclerosant diluted by blood will be washed away and ineffective in damaging the vein wall. In one method of the current invention, the infusion device may be used to deliver sclerosant directly to the vessel wall, thereby minimizing the amount of drug that is diluted by the blood flow. The infusion device is placed at the desired treatment location within the vein. The infusion segment is then expanded to its maximum diameter causing the infusion arms to come in contact with the inner wall. Fluid delivered through the device will exit from the infusion ports located on the expanded arms and come into direct contact with the vessel wall, thereby maximizing the amount of drug delivered to the vessel wall, and reducing the total fluid volume required to achieve treatment success. Optionally, as the vessel collapses, the outer diameter of the infusion segment may be reduced to accommodate the smaller vessel diameter and then the drug delivery may be continued. This method may be repeated to cover longer treatment lengths of veins by segmental treatment and subsequent repositioning of the device along another segment of the vein. Alternatively, a continual pull back method may be used to deliver the drug along the course of a long vein segment.

Figure 3:
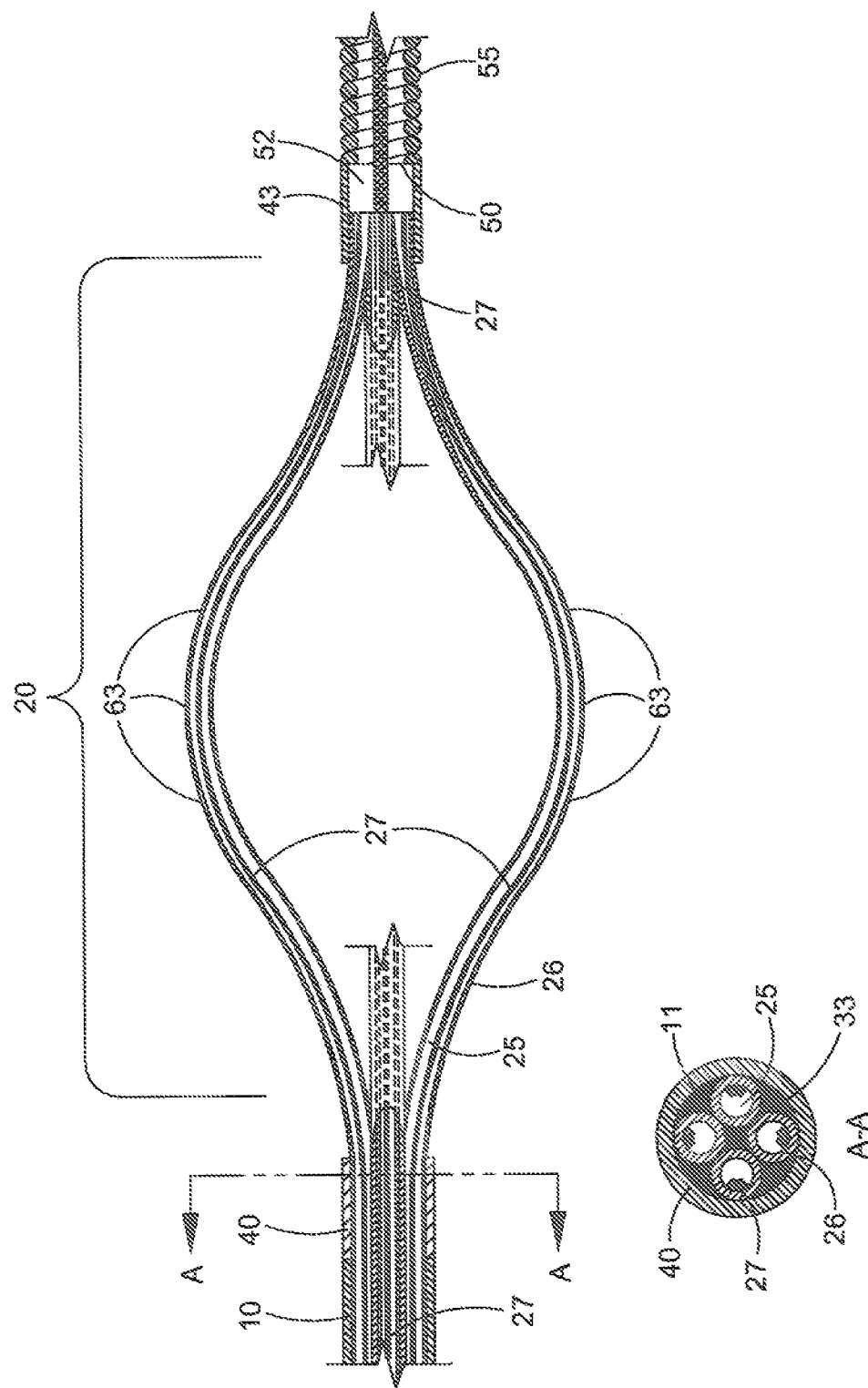
FIG. 3 is a plan view of an alternative embodiment of the fluid delivery device of the current invention shown with the infusion segment in an expanded position.

Referring now to FIG. 3, an alternative embodiment of the current invention is shown in an enlarged partial cross-sectional view. In this embodiment, the infusion device 1 is comprised mainly of a flexible polymer tubing which transitions from a single elongated hollow member 10 to a plurality of flexible, hollow infusion arms 26 which are also comprised of a flexible polymer material. A leading flexible tip 55 is positioned distally of the infusion segment. Nitinol or other shape memory metal wire support elements 27 extend through each lumen 25 of the hollow infusion arms 26. Support elements 27 are pre-formed into expanded infusion segment profile so that when the constraining sleeve or catheter is retracted as previously described, the infusion segment expands to the pre-formed profile as shown in FIG. 3. As shown in Detail A-A of FIG. 3, support elements 27 are positioned within lumens 25 of infusion arms 26, which are coaxially surrounded by and held in position by proximal collar 40. Support elements 27 may be formed of solid shape memory wire elements or they can be formed by longitudinally cutting a metal cannula to form support elements with a wedge-shaped cross-sectional profile as shown in Detail A-A. Support elements 27 may be free-floating within lumens 25 of arms 26 or alternatively, elements 27 may be positioned within the wall of infusion arms 26.

In operation, the fluid delivery system 1 is inserted into the vasculature and advanced to the treatment site using the leading flexible tip 55 to facilitate advancement through the vessel. Once positioned, the restraining sleeve or catheter is retracted which causes the infusion segment 20 to expand radially outward as the individual support elements 27 "spring" into their unrestrained, preformed shapes as shown in FIG. 3. Fluid delivered through the catheter shaft lumen 10 advances through the infusion arms 26 and exits into the targeted tissue via infusion ports slit 63, as described in more detail below.

The polymer shaft embodiment of the infusion device of the current invention is advantageous in several respects. This embodiment may be designed to be larger to treat larger vessels or ducts. In this embodiment a device as large as 20 French may be used to treat thrombus or other diseases in larger vessels and ducts. Smaller embodiment may be used to clear thrombus buildup within implanted medical devices such as dialysis catheters or grafts. Additionally, the device may be used to deliver antibacterial or other treatment drugs to vascular access implants such as central or peripheral catheters. The flexibility of the device provides a non-traumatic, exterior surface which will not damage or otherwise compromise the implanted device when clearing intraluminal obstructions. Using flexible material to coaxially surround the pre-formed support elements enhances the overall structural integrity of the device. In addition, the use of a polymer material allows a greater range of design choices with regarding to the infusion ports as will be described in greater detail with reference to FIG. 6A-6D.

Figure 4:
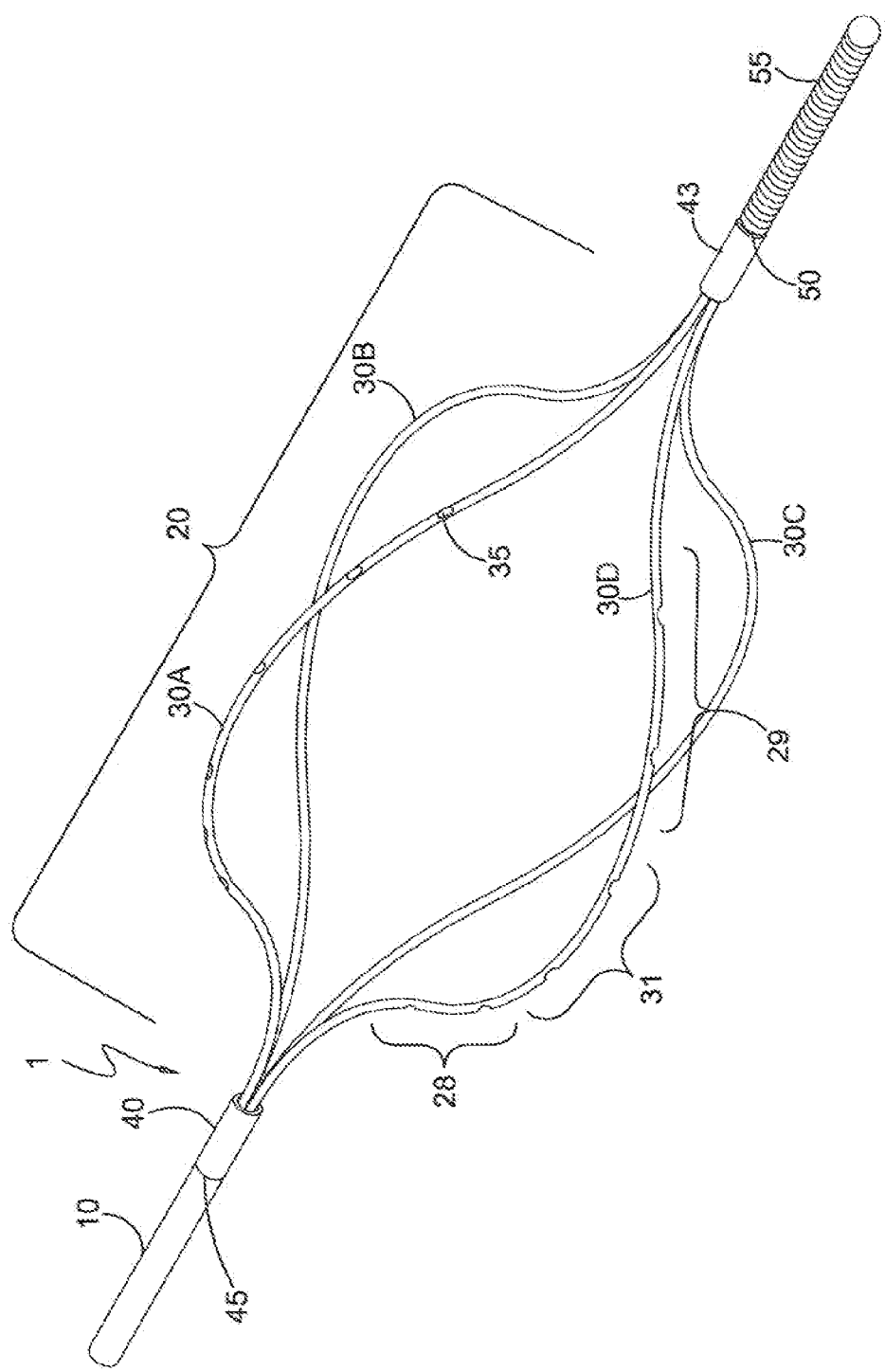
FIG. 4 is an isometric view of the distal section of the fluid delivery device illustrating one embodiment of the infusion segment.

Referring now to FIG. 4, an isometric enlarged view of the distal section of device 1 is shown. Elongated hollow member 10 terminates at collar 40 from which emerge four tubular infusion arms 30A-30D. In one embodiment, the outer diameter of the elongated hollow member 10 is approximately 0.035" with each infusion arm 30A-D being approximately 0.010-0.012". The internal lumen of each infusion arm may be approximately 0.005-0.008". The infusion arms 30A-D expand outwardly at radial segment 28, then transition to a maximum outer diameter at segment 31 before turning radially inward along segment 29. In one embodiment, the infusion arms 30A-D may expand to a maximum diameter of 13-19 mm.

The embodiment of FIG. 4 is designed to allow the infusion device to be inserted through the lumen of an interventional device. As an example, the operator may insert the device of the current invention through the lumen of a standard angioplasty device after the initial angioplasty procedure has been completed. The device may be advanced through the end hole of the angioplasty catheter and positioned within the previously treated vessel segment. The infusion segment of the device of the current invention may then be expanded so as to contact the treated wall. Once positioned, fluid may be delivered to the treated site through the plurality of infusion exits. As an example, restenosis inhibiting agents known in the art may be delivered directly to the treated area through the infusion device. Thus in another aspect of the current invention, the infusion device described herein may be used to provide an adjunctive therapy during a single treatment procedure.

Figure 5:
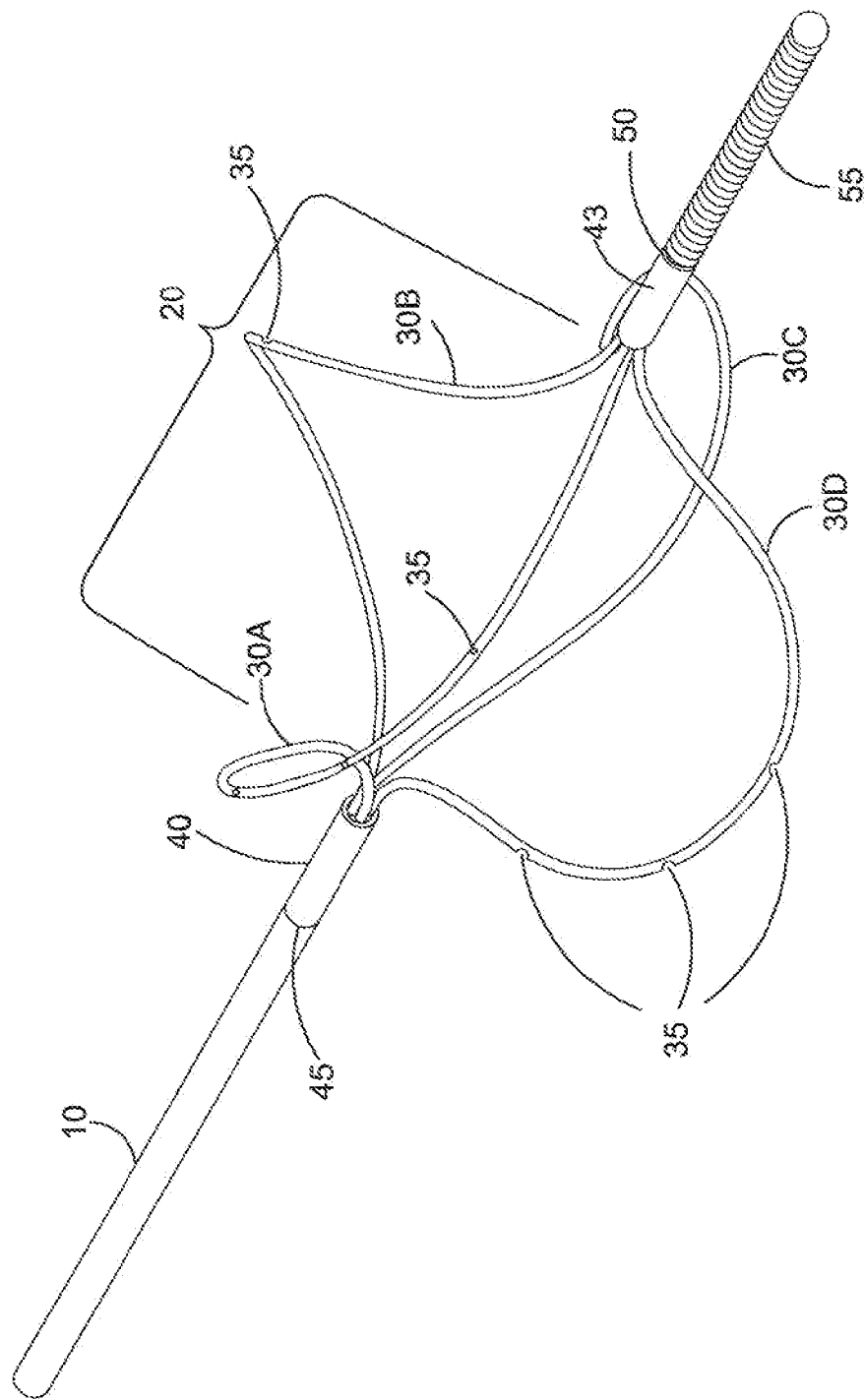
FIG. 5 is an isometric view of the distal section of the fluid delivery device illustrating an embodiment of the infusion segment with twisted infusion arms.

FIG. 5 illustrates an isometric view of yet another embodiment of the current invention. In this embodiment, the individual infusion arms 30A-30D are pre-formed to form a helically shaped infusion segment basket. This embodiment is advantageous when supplementing the drug with mechanical disruption of the clot. The helical shape will aid in the dispersion of the drug along the entire circumference of the inner vessel wall.

Figures 6A, 6B, 6C, 6D:
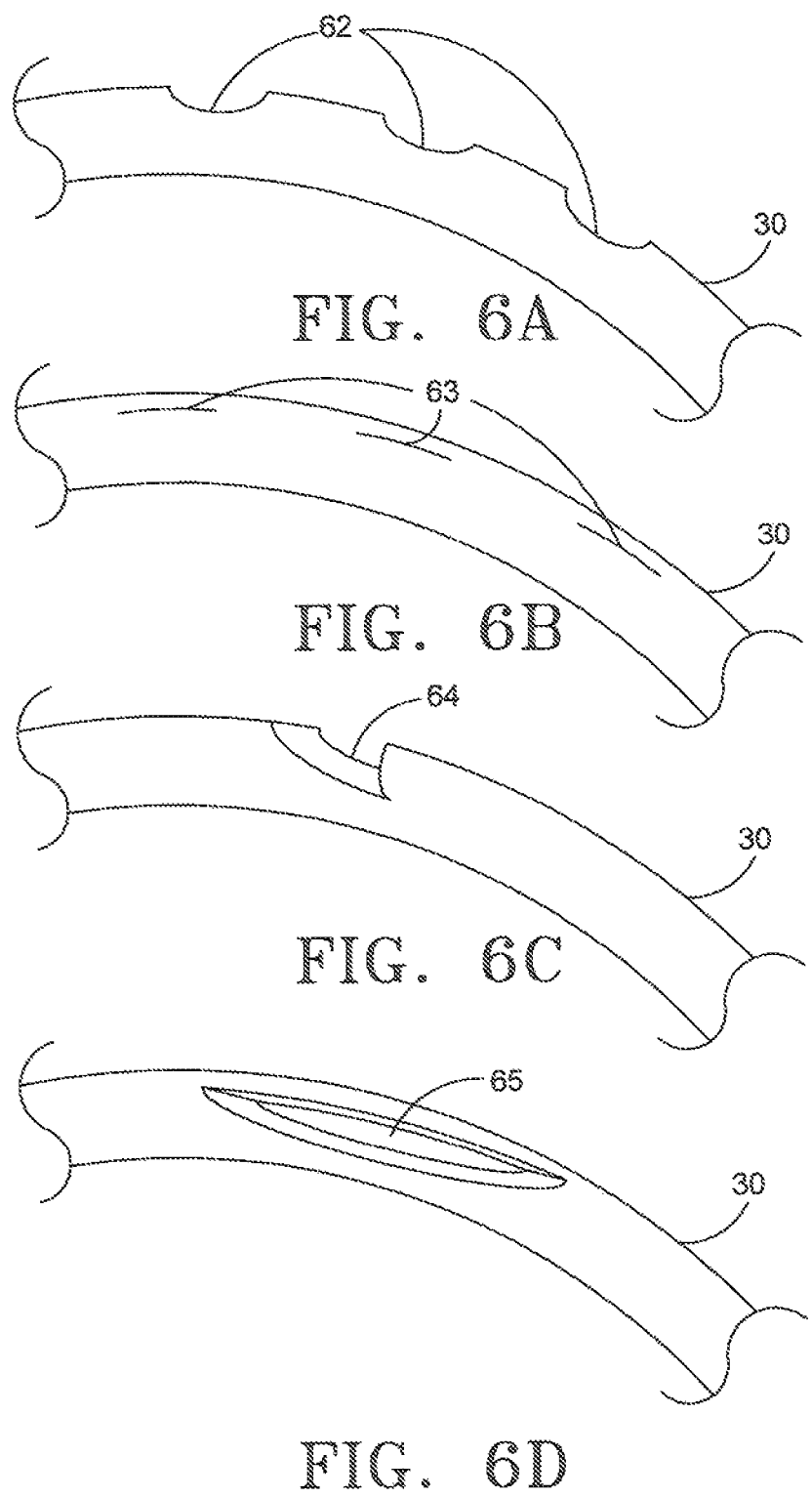
FIGS. 6A-6D are enlarged partial plan views of various embodiments of the infusion ports positioned along an infusion arm.

The configuration of the fluid exit ports positioned along the infusion arms may have several designs as shown in FIG. 6A-6D. The fluid infusion ports 35 can be in the shape of holes 62 as shown in FIG. 6A, slits 63 as in 6B, or various skive designs as shown in FIG. 6C and FIG. 6D. There can be either a single fluid infusion port on each infusion arm 30 or multiple fluid infusion ports on each infusion arm 30 as in FIG. 6A-6D. The fluid infusion ports can be oriented to the inner surface of the infusion arms 30 to direct drugs such as clot dissolving agents into material within the lumen of a vessel. Alternatively, the fluid infusion ports can be oriented to outer surface of the infusion arms 30 to maximize fluid contact with the vessel wall. The slits 63 as seen in FIG. 6B can be used with the polymer embodiment, which is described in further detail below.

As shown in FIG. 6A, a plurality of holes 62 are positioned along infusion arm 30. Holes 62 may be formed using drilling, laser, electrical-discharge machining (EDM) or punch techniques known in the art. The hole diameter may be adjusted so as to control the rate at which the fluid exits the device. For example, the smaller the holes, the higher the velocity at which the fluid is delivered. The holes may also be positioned in a pattern which optimizes dispersion of the fluid along the entire infusion segment.

Referring now the embodiment shown in FIG. 6B, a series of infusion ports 35 are in the form of pressure responsive slits 63 which evenly distribute fluid along the entire infusion length of each arm. The slit designs are disclosed by in U.S. Pat. Nos. 5,250,034 and 5,267,979, both of which are incorporated herein by reference. These pressure responsive slits 63 are in communication with the lumen of the infusion arms 30 and are designed to open under a predetermined pressure created by the introduction of the fluid agent. A relatively low pressure, for example about 1-10 PSI, will "crack" the slits open, which can be used when slowly infusing a fluid. When the present invention is being used to "spray"—such as when delivering a sclerosing agent—there are two different pressure ranges that may be measured as follows. A peak pressure of about 800-900 PSI is the initial pressure in the catheter when the fluid is first delivered into the device. An injection pressure of about 400-500 PSI is the pressure that the fluid flows once the entire device is filled with fluid and is escaping through the slits. The injection of fluid can be powered by a dedicated injector about the size of a standard infusion pump. The slit design is particularly suited for a polymer embodiment. The slits 63 also prevent back flow of material into the fluid delivery and treatment device 1. The length of the slits 63 may range from 0.005-0.030" inches in length and may comprise various slit patterns as is known in the art. Various patterns of fluid infusion port density or length are possible on the same infusion arm 30.

In an example of other infusion port embodiments, the fluid infusion ports may be in the shape of skives 64 or 65, as shown in FIGS. 6C-D, which can be used to direct the flow of the fluids in a particular direction. An additional benefit of using infusion ports in the shape of skives 64 or 65 is that the infusion arms 30 will have a sharpened edge at the point where the infusion arms 30 will contact the vessel wall. Thus, the when the infusion ports are shaped as skives, the infusion segment may be used to simultaneously deliver fluids to the vessel wall while scraping or otherwise abrading the luminal wall. Thus, the skives 64 or 65 may facilitate and enhance the treatment of various conditions. For example, rotation of the device may cause the skives to be scrape a stenotic lesion within a vessel. The collapse of a lumen due to mechanical abrasion of the vessel wall may be achieved by the sharp edges of the skived holes. The mechanical abrasion of the wall may be done prior to, during or after the delivery of fluids, depending on the medical condition being treated.

The skives 64 or 65 may be used to achieve the mechanical maceration of thrombus within a native vessel/graft or implant lumen. The skives may also be used to cause disruption of loculated abscesses to improve complex drainage procedures. With this method, the device of the current invention may be inserted into and through the lumen of a drainage catheter. The device may then be used to deliver antibiotic or other fluid after which the infusion segment may be rotated to disrupt/break up loculations within the abscess. In another example, the device may be used to supplement tumor treatment by the delivery of chemotherapeutic or ablative agents (such as alcohol) to the targeted tumor. Alternatively, conductive fluid such as saline may be delivered to the tumor volume prior to or during the delivery of either thermal energy or non-thermal electrical pulses to achieve irreversible electroporation, as is known in the art. In yet another embodiment of the method of this invention, the device may be designed so as to deliver occlusion agents and/or abrasive action to fallopian tubes for closure.

Figure 7A:
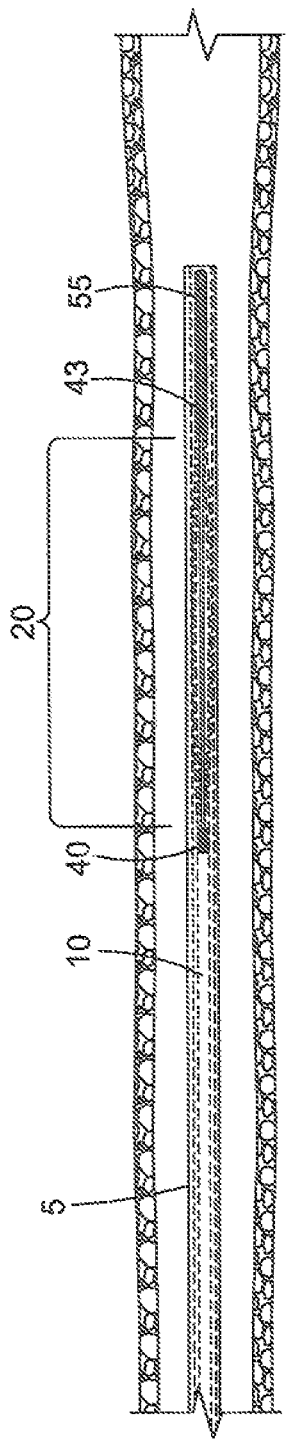
FIGS. 7A-7B depict the fluid delivery device within a vessel segment.
Figure 7B:
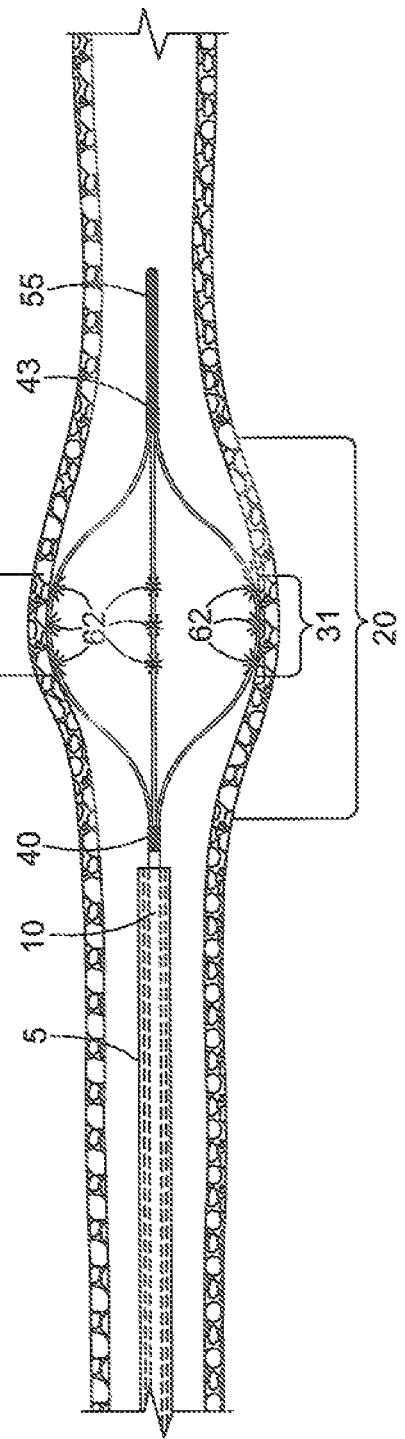

FIG. 7A-7B illustrates one method of using the device of the current invention. In FIG. 7A the device 1 is in shown being delivered to the intended treatment site. In one embodiment, the device 1 will fit within the lumen of a procedure catheter or sheath 5. When the device 1 is within the lumen of the procedure sheath the expandable infusion/treatment segment 20 is in a collapsed or compressed position. As seen in FIG. 7B, the procedure sheath 5 may be retracted proximally, so that the entire expandable infusion/treatment segment 20 is fully exposed and expanded. After the expandable infusion/treatment segment 20 has fully expanded and is in contact with the vessel wall 31 the device is ready to deliver the intended fluids and/or provide mechanical treatment, as previously described.

Figure 7C:
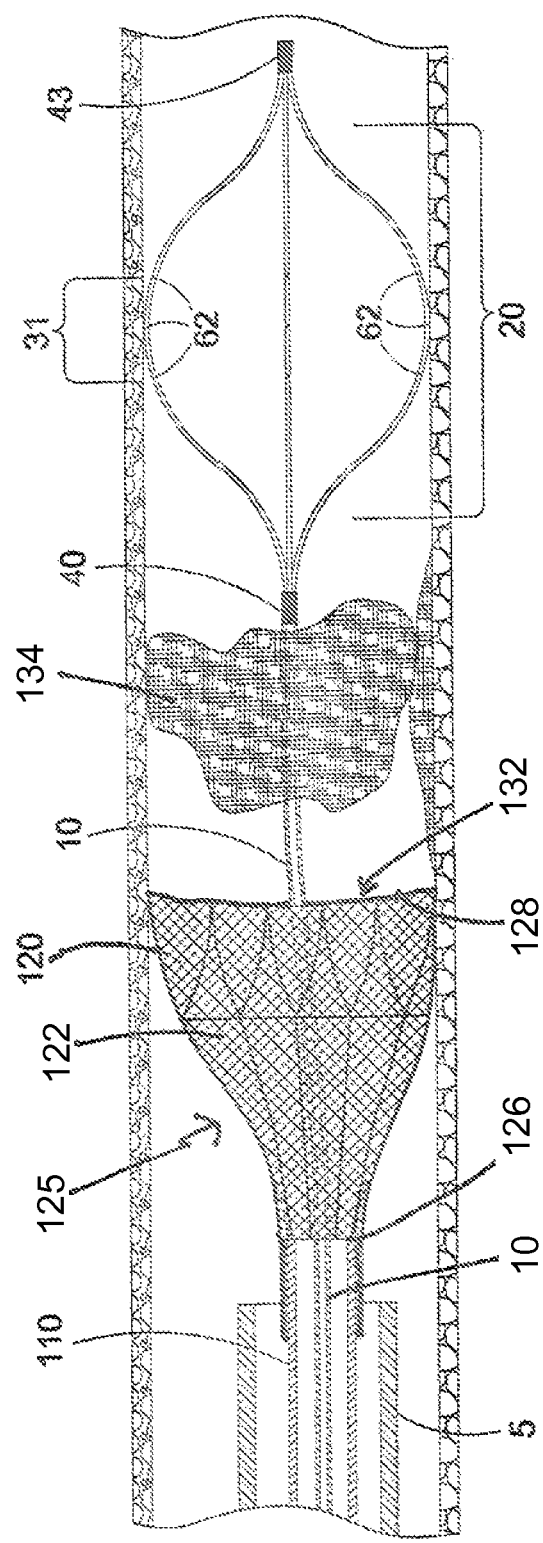
FIGS. 7C-7D are plan views of an alternative embodiment of the fluid delivery device including an expandable capture sheath.

FIG. 7C illustrates another embodiment of the infusion device which includes an expandable capture sheath 125 consisting of an elongate shaft 110 having an expandable cone member 120 disposed at a distal end thereof. The expandable capture sheath 125 is positioned over the infusion device and within the lumen of the procedure sheath 5. Elongate shaft 110 is sized to be disposed within and move independently of procedural sheath 5, and elongated hollow member 10 of the infusion device is sized to be disposed within and move independently of the elongate shaft 110. The purpose of the expandable sheath 125 is to collect and capture pieces of the thrombus for removal from the vessel.

Elongated shaft 110 can be made of materials similar to those of elongated hollow member 10, as described above. Expandable cone member 120 can be made from a plurality of nitinol wire members 122 encased with a permeable material bonded thereto. In the preferred embodiment expandable cone member 120 is a funnel shape. The nitinol wire members 122 can be covered with an impervious material or formed as a tight mesh so the expandable cone member 120 can capture smaller pieces of the thrombus. Each wire member 122 of the expandable cone member 120 includes a proximal end 126 and distal end 128. Adjacent proximal ends come together and may be welded, or bonded using an epoxy to elongate shaft 110. Adjacent distal ends 128 converge to form a leading edge defining an open mouth 132 of expandable cone member 120. The expandable cone member 120 can also be made from a wire mesh encased with a permeable material bonded thereto.

Figure 7D:
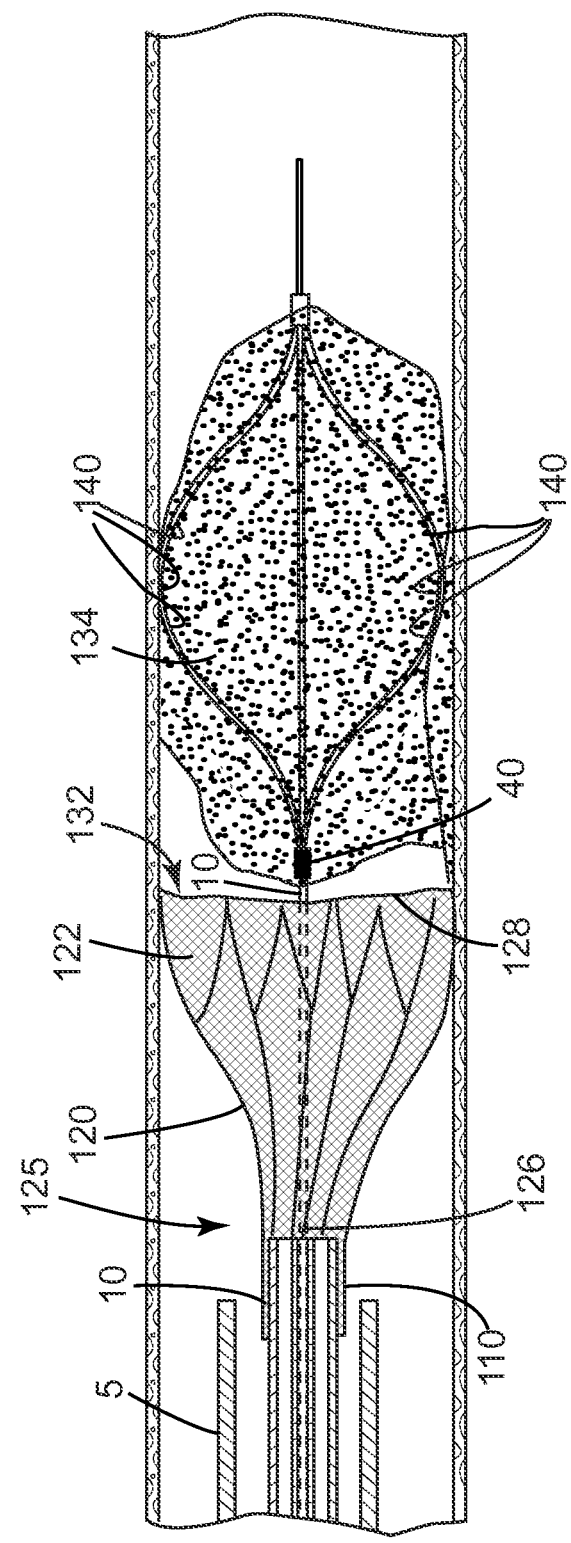

When in use, the expandable cone member 120 is collapsed within a procedure sheath 5 and the expandable infusion/treatment segment 20 is collapsed within the elongated shaft 110 of the expandable cone member 120 (not shown). The expandable infusion/treatment segment 20 is moved into position either distally of the thrombus as shown in FIG. 7C, or within the clot as shown in FIG. 7D. The expandable cone member 120 is advanced distally to thrombus 134 while expandable infusion/treatment segment 20 is held stationary. Alternatively, the procedure sheath 5 can be proximally retracted allowing the expandable cone member 120 to self-expand or mechanically expanded.

As seen in FIG. 7D, the infusion device delivers fluids via exit ports 140 into thrombus 134 using an intended drug such that the clot is softened and prepared for removal. To supplement the drug lysis action, the expandable infusion/treatment segment 20 may be manipulated as previously described to further disrupt the thrombus through mechanical action. The softened thrombus 134 may be dragged into the expandable cone member 120 (with or without aspiration on funnel sheath) by retracting the expandable infusion/treatment segment 20. Alternatively, the expandable infusion/treatment segment 20 can be used to hold the thrombus 134 stationary while distally advancing the expandable cone member 120 (with or without aspiration on funnel sheath) to capture the thrombus. Once the softened thrombus 134 has been captured within the expandable cone member 120 the expandable infusion/treatment segment 20 and expandable sheath 125 may be retained by the procedural sheath 5 for removal. Additionally, the removal of the thrombus 134 may be facilitated using standard aspiration techniques.

FIG. 7E illustrates yet another embodiment of the infusion device which includes an expandable capture sheath 225, an expandable infusion/treatment segment 20A, and an embolic protection device 222. The infusion device shown in FIG. 7E may be used for placement over a guide wire GW or may include a leading flexible tip (not shown). The leading flexible tip (not shown) is similar to the leading flexible tip 55 of FIG. 2C and also facilitates tracking and advancement of device 1 through the vessel or alternatively through the lumen of a catheter or other treatment device.

The expandable capture sheath 225 is similar to expandable sheath 125 (see FIG. 7D) and is also used to collect and capture pieces of the thrombus for removal from the vessel. The expandable sheath 225 consists of an elongate shaft 210 having an expandable capture member 220 disposed at a distal end thereof. In the embodiment shown, the expandable capture member includes a cone-shaped portion, however other shapes can be used, such as cup-shaped, square-shaped, funnel-shaped, ellipse-shaped, etc. In the embodiment shown, the length of the expandable capture member is less than the length of the treatment segment 20A. In other embodiments, the length of the expandable capture member can be equal to or greater than the length of the treatment segment, such that it is sufficiently-sized to receive and restrain the treatment segment.

Proximal coupler 226A is attached to an elongate shaft 228. In the instance of over-the-wire placement, the distal coupler 226B is open and free to receive a guidewire GW therethrough. When the infusion device includes the leading flexible tip (not shown), the distal coupler 226B is connected to the leading flexible tip. The expandable capture sheath 225 is positioned over the infusion device and within the lumen of the procedure sheath 5 (see FIG. 7D). Elongate shaft 210 may be sized to be disposed within and move independently of procedural sheath, and elongated hollow member 10 of the infusion device may be sized to be disposed within and move independently of the elongate shaft 210 of expanding sheath 225. Elongate shaft 228 may be sized to be disposed within and move independently of elongate hollow member 10, elongate shaft 210 and procedural sheath. However, it is also conceivable that elongate shaft 210 of expanding sheath 225 and elongate shaft 228 of embolic protection device 222 can be securely attached to one another and move in unison.

The treatment segment 20A includes at least one radially expandable arm 30 with at least one exit port (see FIGS. 6A-6D) for delivering fluid. Embolic protection device 222 includes a radially expandable filter 224 consisting of a plurality of intermeshed wires connected by a proximal coupler 226A and a distal coupler 226B. During infusion clot particles may break away from the thrombus and move downstream, causing potential embolisms. The intermeshed wires of the radially expandable filter 224 are formed specifically to catch these smaller masses of clots that tend to break away and move downstream. As such, the purpose of the embolic protection device 222 is to collect and capture the smaller pieces of thrombus that may potentially remain after infusion and before removal of the device from the vessel. The embolic protection device can capture particles larger than 3 mm for venous, A/V applications. In one embodiment, the embolic protection device can be replaced by an expandable balloon or finer filter for arterial applications.

Figure 7F:
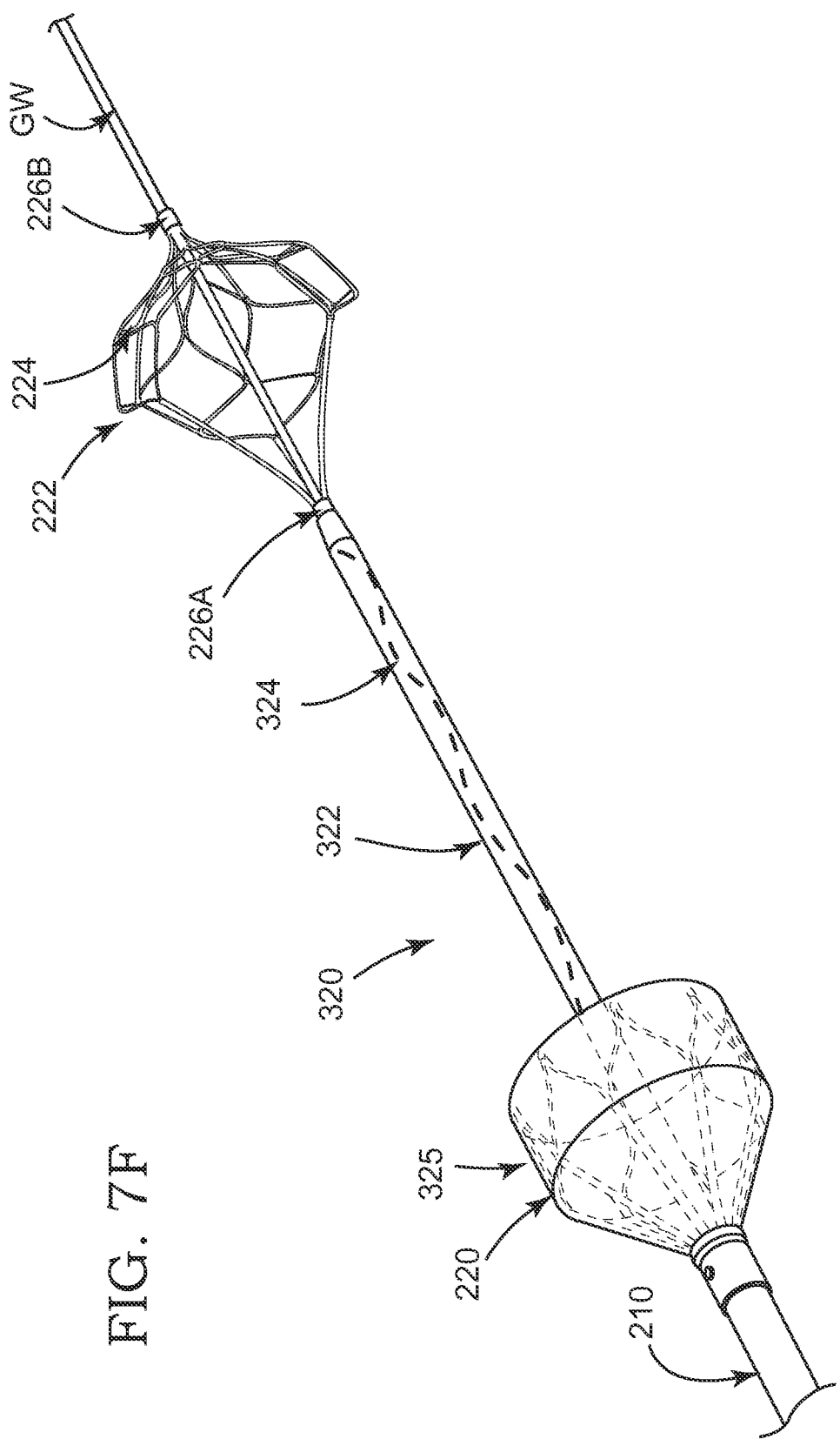
FIG. 7F is a partial isometric view of yet another embodiment of the fluid delivery device including a tubular infusion segment.

FIG. 7F illustrates yet another embodiment of the infusion device which includes an expandable capture sheath 325, a non-expandable tubular infusion/treatment segment 320, and embolic protection device 222. Similar to the infusion device of FIG. 7E, the infusion device shown in FIG. 7F may also be used for placement over a guide wire GW or may include a leading flexible tip (not shown). The expandable capture sheath 325 is similar to expandable sheaths 125 (see FIG. 7D) and 225 (see FIG. 7E). The leading flexible tip (not shown) is also similar to the leading flexible tip 55 of FIG. 2C. In both instances, either over-the-wire placement of the infusion device or the infusion device with the leading flexible tip (not shown), the embolic protection device 222 of FIG. 7F is similar to the embolic protection device 222 of FIG. 7E and functions to collect and capture the smaller pieces of the thrombus 134 that may potentially remain after infusion and before removal of the device from the vessel.

The non-expandable tubular infusion segment 320 is similar to those disclosed in U.S. Pat. Nos. 5,250,034 and 5,267,979, both of which are incorporated herein by reference. The infusion segment is comprised of a tubular elongated shaft 322 with exit ports 324 positioned along the portion of the shaft extending beyond the expandable cone member 220. Fluid entering the proximal end of the shaft (not shown) will exit from the plurality of exit ports 324 to contact the thrombus 134 (see FIG. 7D) or other obstruction. The exit ports 324 may be holes or pressure responsive slits as described in the above referenced patents. The expandable capture sheath 325 is positioned over the non-expandable tubular infusion segment 320 and within the lumen of the procedure sheath 5 (see FIG. 7D). Elongate shaft 310 is sized to be disposed within and move independently of procedural sheath, and the non-expandable tubular infusion segment 320 is sized to be disposed within and move independently of the elongate shaft 310 of the expandable capture sheath 325. Elongate shaft 228 of the embolic protection device 222 is sized to be disposed within and move independently of the non-expandable tubular infusion segment 320, elongate shaft 310 and procedural sheath 5.

However, it is also conceivable that elongate shaft 210 of expanding sheath 225 and elongate shaft 310 of non-expandable tubular infusion segment 320 can be securely attached to one another and move in unison. The purpose of the non-expandable tubular infusion segment 320 is to provide the infusion device with higher pressured pulsed spray jets or pressure responsive slits that open in unison and are capable of delivering fluid at high pressures to aggressively aid in disrupting/breaking up the obstructions. The pressure of fluid injected into the non-expandable tubular infusion segment 320 embodiment may be up to 800 pounds per square inch (PSI) for high pressure infusion of lytic or other fluid. However, the pressure required to open the exit ports 324 or pressure responsive slits, known in the art as the cracking pressure, may be 5-10 PSI. At a pressure range of 5-10 PSI the fluid being delivered will weep or be slowly dripping from the exit ports 324 which may be used for a slow infusion of lytic or other fluid. In one embodiment, the pressure responsive slits are designed to remain closed at a pressure of 50 PSI or below.

The infusion devices of both FIGS. 7E and 7F operate similar to the infusion device of FIG. 7C; however, either the expandable infusion/treatment segment 20A or the non-expandable tubular infusion segment 320 is used to inject lysis and disrupt the thrombus 134 (see FIG. 7C). When in use, the expandable capture member 220 is collapsed within a procedure sheath 5 (see FIG. 7C) and the expandable infusion/treatment segment 20A is collapsed within the elongated shaft 210 of the expandable capture member 220 or the non-expandable tubular infusion segment 320 is positioned within the elongate shaft 210. The expandable infusion/treatment segment 20A or the tubular infusion segment 320 is moved into position, using the over-the-guide wire approach or using the embodiment with the leading flexible tip 55, either distally of the thrombus, similar to the infusion device as shown in FIG. 7C, or within the clot as shown in FIG. 7D. The expandable cone member 220 is advanced distally to thrombus while expandable infusion/treatment segment 20A or the non-expandable tubular infusion segment 320 is held stationary. The embolic protection device 222 is moved into position and is advanced distally of the thrombus.

Similar to the method as shown in FIG. 7D, the infusion devices of FIGS. 7E and 7F deliver fluids 140 into thrombus 134 using an intended drug such that the clot is softened and prepared for removal. In the case of the expandable infusion/treatment segment 20A, to supplement the drug lysis action, the expandable infusion/treatment segment 20A may be manipulated as previously described to further disrupt the thrombus 134 (see FIG. 7D) through mechanical action. However, with the case of the non-expandable tubular infusion segment 320, the high pressure of the injector disrupts the thrombus. For example, if high pressure injection through the non-expandable tubular infusion segment 320 is required to disrupt the clot the injection pressure can range from 300-800 PSI. However, if low pressure injection through the non-expandable tubular infusion segment 320 is required for a slow infusion of fluid into the clot the injection pressure can range from 5-10 PSI. At this point, when using the non-expandable tubular infusion segment 320, the embolic protection device 222 is ready to be pulled back and capture the softened thrombus and any remaining clot particles. However, when using the expandable infusion/treatment segment 20A, after the thrombus has been softened and prior to pulling back the embolic protection device 222, an additional step is required wherein the softened thrombus is dragged into the expandable capture member 220 (with or without aspiration on funnel sheath) by retracting and collapsing the expandable infusion/treatment segment 20A. If aspiration is used, the expandable capture member, such as an inflatable balloon, can be sufficiently sized such that when it is expanded, it occludes the blood vessel and reduces blood flow into and through the clot, which will improve aspiration by focusing the suction on the clot, not the blood. Now, in both instances, the embolic protection device 222, and expandable infusion/treatment segment 20A or the non-expandable tubular infusion segment 320 are ultimately received into the expandable capture member 220 for removal of the thrombus. This can be done by either retracting the embolic protection device 222 and expandable infusion/treatment segment 20A or the non-expandable tubular infusion segment 320 into a stationary expandable cone member 220 or advancing the expandable cone member 220 toward a stationary embolic protection device 222 and expandable infusion/treatment segment 20A or the non-expandable tubular infusion segment 320. Once the softened thrombus has been captured within the expandable cone member 220, the expandable infusion/treatment segment 20A or non-expandable tubular infusion segment 320 and expandable sheath 225, 325 may be retained by the procedural sheath 5 (see FIG. 7D) for removal. Additionally, high pressure injections may also be used using a pulsed spray injector and standard syringe. The embodiments as detailed in FIGS. 7E and 7F may be used to achieve the mechanical maceration of thrombus within a native vessel/vein/artery/graft/fistula or implant lumen.

Figure 8:
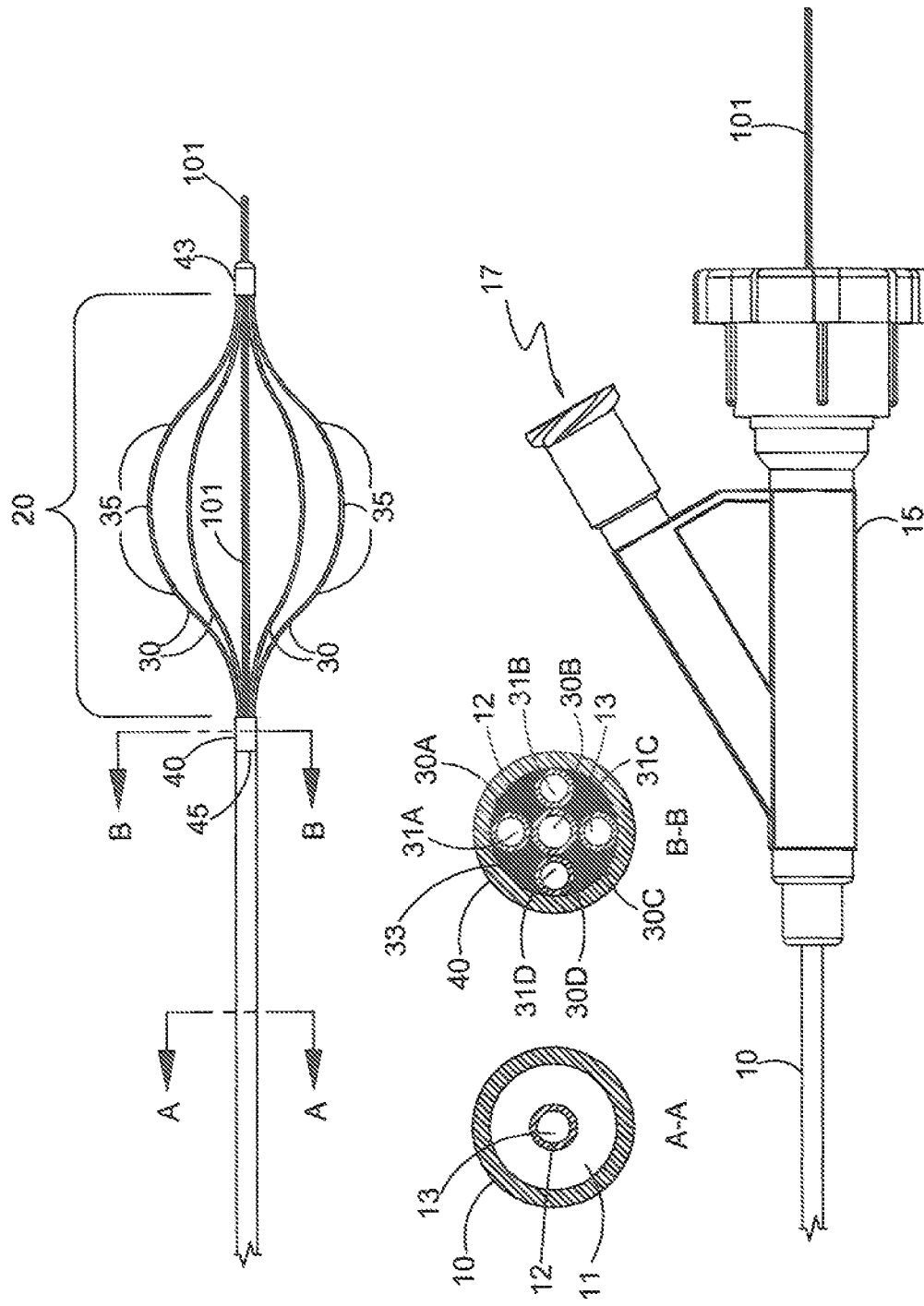
FIG. 8 is a partial plan view of an embodiment of the fluid delivery device designed to be advanced over a standard guidewire.

FIG. 8 illustrates another embodiment of the infusion device designed to be used with a standard guidewire. The leading flexible tip 55 of FIG. 1 has been replaced with a distal tip section having a through lumen which allows the entire device to be backloaded over a standard guidewire 101. The elongated hollow member 10 extends from Y-connector 15 distally to the expandable infusion segment 20. As shown in cross-section A-A of FIG. 8, within single through lumen 11 of elongated hollow member 10 is a dedicated guidewire lumen 13 which extends distally from the Y-connector and terminates at the distal edge of collar 40. The side arm port 17 is in fluid communication with lumen 11 of elongated hollow member 10, providing a fluid path from the Y-arm of the connector 15 to the infusion arm lumens 31A-31D. As shown in "B-B", dedicated guidewire lumen 13 is coaxially surrounded by infusion arms 30A-30D. Collar 40 coaxially surrounds and constrains the infusion arms. The Y-connector 15 may include a Touhy-Borst assembly, which is a gasket assembly used for holding and sealing around guidewires or other interventional devices. The guidewire compatible design shown in FIG. 8 may be sized to be used with guidewires of various sizes ranging from 0.014-0.045".

In an alternative embodiment the coaxially-positioned guidewire tube 12 may extend distally from the distal most end of the proximate collar 40 to the distal end of collar 43. Lumen 13 of guidewire tube 12 provides a pathway for the guidewire along the entire length of the device.

In operation, the device of FIG. 8 is loaded over a guidewire by first collapsing the device infusion segment inside an insertion tool (tube) and then threading the proximal most end of guidewire 101 into the distal end hole of the device at distal collar 43. The guidewire 101 is advanced until it exits Y-connector 15, as shown in FIG. 8. The insertion tool can then be used to insert the collapsed distal infusion segment through the hub of a procedural catheter or sheath.

FIG. 9 shows a flow chart of a method for removing a thrombus from a blood vessel according to one embodiment of the invention. At step 901, the blood vessel is accessed via the Seldinger technique (0.035" wire) and a 5F sheath is inserted. At step 902, the treatment segment having infusion holes is positioned in the thrombus, wherein the infusion holes are engineered to operate at high pressure and deliver a uniform amount of saline/lytic agent from each hole. The infusion length of the treatment segment is a minimum of 5 cm with a maximum length equivalent to the thrombus length. At step 903, at least 1 cc ml of saline bolus is forcefully injected with a velocity that is sufficient to macerate the thrombus. The saline bolus may consist of 0.2 mg/ml mixture of recombinant tissue plasminogen activator (rtPA) and saline pulsed every 5 seconds for 10 minutes or less with an injection pressure of 1-3 kpsi. At step 904, the user waits for 20-30 minutes and imaging is used to determine the progress of thrombus lysis. (No waiting for A/V or other acute applications.) At step 905, if the thrombus is resolved, then proceed to step 909, and if the thrombus is not resolved, then proceed to step 906. At step 906, the sheath is upsized and aspirate with 8F wide mouth catheter or sheath, and the embolic capture device is used to pull any residual thrombus into the sheath. At step 907, if the thrombus is resolved, then proceed to step 909, and if the thrombus is not resolved, then proceed to step 908. At step 908, the wide mouth catheter is removed and catheter directed thrombosis (CDT) is performed for less than 24 hours. At step 909, the devices are removed from the vessel and imaging is used to confirm vessel patency. The procedure time can be about 1-3 hours in an interventional radiology suite for deep venous thrombosis, and about 15 minutes for A/V applications.

The fluid delivery and treatment device of the present invention is designed to be used in a variety of body lumens, including but not limited to veins, arteries, ducts, brachial tubes, esophagus, or any other vessel that requires the delivery of drugs or fluids. As used herein, the term "blood vessel" can refer to an artificial blood vessel, such as a graft. The device can be used to deliver a variety of medical preparations including therapeutic agents and diagnostic agents for therapeutic or diagnostic purposes.

The above disclosure is intended to be illustrative and not exhaustive. This description will suggest many modifications, variations, and alternatives may be made by ordinary skill in this art without departing from the scope of the invention. Those familiar with the art may recognize other equivalents to the specific embodiments described herein. Accordingly, the scope of the invention is not limited to the foregoing specification.

We claim:

1. A medical device for removing material from a hollow anatomical structure, comprising:
    a radially expandable capture member;
    a treatment segment positioned distally of the capture member in use, the treatment segment includes a plurality of expandable arms wherein each expandable arm includes the at least one exit port, each expandable arm includes an infusion lumen adapted for delivering a fluid agent to the material through the at least one exit port;
    an embolic capture device positioned distally of the treatment segment in use and including a radially expandable filter for capturing a part of the material which travels downstream of the treatment segment.

2. A medical device of claim 1, wherein the material is a thrombus.

3. A medical device of claim 1, wherein the treatment segment includes at least one radially expandable arm.

4. A medical device of claim 1, wherein the treatment segment is adapted to be used over a guidewire.

5. A medical device of claim 3, wherein the at least one radially expandable arm is adapted to rotate to mechanically disrupt the material.

6. A medical device of claim 1, further comprising a tension wire for controlling the amount of radial expansion of the plurality of expandable arms.

7. A medical device of claim 1, wherein the radially expandable capture member includes a plurality of wire members containing a memory-shape material.

8. A medical device of claim 1, wherein the radially expandable capture member is independently movable in a longitudinal direction in relation to the treatment segment.

9. A medical device of claim 1, wherein the radially expandable capture member is independently movable in a rotational direction in relation to the treatment segment.

10. A medical device of claim 1, wherein the treatment segment includes an elongate shaft and the at least one exit port is located on the elongate shaft.

11. A medical device of claim 1, further comprising a vacuum source connected to the radially expandable capture member for capturing the material for removal.

12. A medical device of claim 1, wherein the at least one exit port includes at least two pressure responsive slits that are designed to open at the same injection pressure.

13. A medical device of claim 12, wherein the injection pressure required to open the pressure responsive slits is about 5 PSI.

14. A medical device of claim 1, wherein the radially expandable filter includes a plurality of intermeshed wires.

15. A method for removing material from a hollow anatomical structure, comprising:
    inserting a removal device including a radially expandable capture member, a treatment segment having a plurality of expandable arms wherein each expandable arm includes the at least one exit port, each expandable arm includes an infusion lumen, and an embolic capture device having a radially expandable filter;
    positioning the treatment segment near the material such that the expanded filter is positioned distally of the treatment segment and the expanded capture member is positioned proximally of the treatment segment, the expanded filter capable of capturing a part of the material which travels downstream of the treatment segment;
    injecting a fluid agent to the material through the exit port;
    receiving the treatment segment in the expanded capture member; and
    receiving the embolic capture device in the expanded capture member.

16. A method of claim 15, wherein the treatment segment includes at one radially expandable arm, and further comprising:
    rotating the treatment segment to mechanically disrupt the material prior to removal.

17. A method of claim 15, wherein the step of injecting includes:
    delivering a lytic agent through the exit port to chemically disrupt the material prior to removal.

18. A method of claim 15, further comprising:
    applying suction to draw the material into the radially expandable capture member prior to removal of the material.

19. A method of claim 15, wherein the fluid agent consists of a mixture of saline and recombinant tissue plasminogen activator.

20. A method of claim 15, further comprising injecting a bolus of the fluid agent through the plurality of exit ports until the material has been dissolved.

* * * * *